United States Patent [19]

Kötzsch et al.

[11] 4,310,680

[45] Jan. 12, 1982

[54] METHOD OF CLEAVING SILOXANES

[75] Inventors: Hans-Joachim Kötzsch, Rheinfelden;
Jürgen Amort, Troisdorf;
Hans-Joachim Vahlensieck, Wehr, all
of Fed. Rep. of Germany

[73] Assignee: Dynamit Nobel AG, Troisdorf, Fed. Rep. of Germany

[21] Appl. No.: 215,488

[22] Filed: Dec. 11, 1980

[30] Foreign Application Priority Data

Dec. 13, 1979 [DE] Fed. Rep. of Germany ....... 2950030

[51] Int. Cl.³ ............................. C07F 7/08; C07F 7/18
[52] U.S. Cl. ................................. 556/467; 556/406; 556/453; 556/462
[58] Field of Search ................ 556/453, 462, 406, 467

[56] References Cited

U.S. PATENT DOCUMENTS

| | | | |
|---|---|---|---|
| 2,759,009 | 8/1956 | Brimm | 556/467 |
| 3,631,085 | 12/1971 | Krahnke et al. | 556/453 |
| 3,689,519 | 9/1972 | LeFort | 556/467 X |
| 3,718,682 | 2/1973 | Bakassian et al. | 556/467 |

*Primary Examiner*—Paul F. Shaver
*Attorney, Agent, or Firm*—Sprung, Felfe, Horn, Lynch & Kramer

[57] ABSTRACT

A process for the preparation of a halogen silane and an aromatic compound having at least one —C=O— of

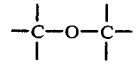

group, while simultaneously effecting cleavage of a siloxane by contacting a compound having at least one aromatically bound mono and/or dihalogen methylene group or an aromatic compound having a mono-, di and or trihalogen methyl group of the formula

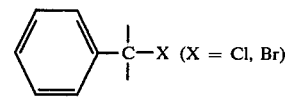

wherein the aromatic moiety can be optionally otherwise substituted, with a siloxane of the formula

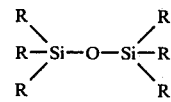

wherein each R moiety is independently selected from the group consisting of halogen, alkyl, alkenyl and O-SiR₃, wherein such R moiety is halogen, alkyl or alkenyl, wherein at least two of the R moieties can, together with the silicon atom to which they are attached, form a ring, at an elevated temperature in the presence of a catalytic amount of a metal or a metal compound, which metal is of the sub-group of elements or of the 5th principal group of the periodic system of the elements, together with a proton donor, or in the presence of a catalytic amount of an oxygen acid.

29 Claims, No Drawings

METHOD OF CLEAVING SILOXANES

BACKGROUND OF THE INVENTION

1. Field of the Invention

The subject matter of the present invention is a method wheeby chlorosilanes can be obtained simultaneously with aromatic aldehydes or caroboxylic acid chlorides or ethers, without substantial production of by-products.

2. Discussion of Prior Art

Chlorosilanes, carboxylic acid chlorides and aromatic aldehydes are known intermediates used in many technical syntheses for the production of silylation products or protective-group reagents, as well as dyes, pharmaceutical products and scents.

Chlorosilanes are produced in technical amounts in the process known as "Rochow synthesis." One disadvantage of this process is the inhomogenity of the products, which necessitates fractional distillation, resulting in a large amount of useless by-products.

Aromatic aldehydes and carboxylic acid chlorides are prepared technically by the reaction of chloromethylbenzenes with water or aromatic carboxylic acids in the presence of catalysts, with the splitting off of hydrogen chloride. In these processes the performance of the hydrolysis presents technical difficulties, or it is necessary to use as starting products the carboxylic acids prepared by separate steps of the process, thereby making the overall process very expensive. All of the processes additionally have the great disadvantage that the hydrogen chloride formed in the reaction has to be removed from the reaction vessel and then subjected to an absorption and/or purification. Furthermore, the hydrogen chloride in many of the above-named reaction products, such as 3-chlorophthalide, for example, results in a loss of storage life. It must, therefore be completely removed from the reaction product. This additional procedure often requires a great deal of work.

Furthermore, many of the applications of the siloxanes or silicones or of the trialkylsilyl compounds suffer from the fact that in them by-products are produced for which there are not many uses. Such unusable by-products are formed in the synthesis of antibiotics, for example (e.g., cephalosporin derivatives) on account of the protection of sensitive groupings by silyl groups in the form of hexamethylsiloxanes, or they are formed in the use of siloxanes as hydraulic oils or heat transfer agents in the form of used or contaminated oil. Often these by-products have to be destroyed, because working them up by the known cleavage of siloxanes with hydrogen chloride in the presence of sulfuric acid or aluminum chloride requires a great deal of trouble and is not optimal.

The problem therefore existed of utilizing the by-products and of recycling them into the process insofar as possible. Furthermore, it has been a long-standing problem to improve the technical preparation of alkyl chlorosilanes and to make them independent of the Rochow synthesis and its disadvantages. The third problem to be solved was the development of a process for the preparation of aromatic carbonyl compounds from chlorinated methylbenzenes, in which the hydrogen chloride that is produced is directly utilized.

SUMMARY OF THE INVENTION

It is an object of this invention, therefore, to provide a process for the preparation of halogens, silanes, and aromatic compounds, having at least one of the following of groups

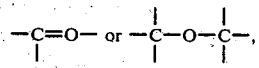

while cleaving siloxanes. It is a further object of this invention to provide a solution to the long-standing problem of providing a commercially suitable process for alkyl chlorosilane production which is not dependent upon the Rochow synthesis and is not encumbered by its disadvantages. It is a further object of this invention to provide a commercially suitable process for the preparation of aromatic carbonyl compounds from chlorinated methyl benzenes in which the hydrogen chloride that is produced is directly utilized.

These and other objects are provided by a process in which siloxanes are cleaved and halogensilanes and aromatic compounds having at least one

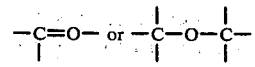

group is provided, which process comprises contacting at least one aromatically bound mono and/or dihalogen methylene group or a compound having mono-, di and-/or trihalogen having mono- di and/or trihalogen methyl group on an aromatic ring which compound has the formula

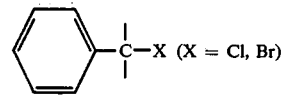

wherein the aromatic moiety can, if desired, also be otherwise substituted, with a siloxane of the general formula

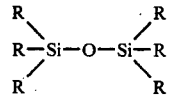

wherein each R moiety independently represents halogen, alkyl, alkenyl or O-SiR$_3$, wherein R has the meaning given above, or at least two of the R moieties can, together with the silicon atom to which they are bound form a ring, at elevated temperature in the presence of a catalytic amount of a metal or a mixture of metals of the sub-group elements or of the 5th principal group of the periodic system of elements, together with a proton donor, or in the presence of a catalytic amount of an oxygen acid or sulfur.

In the formula given above for the siloxanes R is halogen, alkyl, alkenyl, or O-Si R$_3$, wherein R$_3$ in turn is halogen, alkyl, or alkenyl. Where any R moiety is alkyl it is preferably alkyl having 1 to 8 carbon atoms, more preferably 1 to 4 carbon atoms. Where R is alkenyl it is preferred that it have 2 to 8 carbon atoms, particularly 2 to 4 carbon atoms. Where R is halogen, it is preferred that the halogen be chlorine.

By the process of the invention one can cleave siloxanes by the use of halogen methyl aromatic compounds without the occurrence of appreciable by-products. In this process, commercially useful and valuable end products are formed in a high purity from the siloxane and from the halogen methyl aromatic compounds. Hydrogen chloride contamination does not occur, or occurs only to a slight extent.

The procedure of the invention can be performed with virtually all siloxanes, so that halogen silanes can be obtained with selected substituents, depending on the siloxanes that are used as starting material.

The halogen methyl benzenes which can be used in accordance with the invention include mono-, di and trihalogen methyl benzenes, independently of how many halogenated methyl groups are on the benzene ring and in which position with respect to one another. In the case of the monohalogen methyl benzenes, however, lesser yields of the desired end product can be formed, depending on the starting substance. The principle of the newly discovered reaction is, however, also applicable to these compounds.

The aromatic nucleus is preferably not otherwise substituted. In several cases ist may be substituted by one or more halogen atoms, e.g. chlorine or bromine.

The reaction of the invention can be summed up in the following equations.

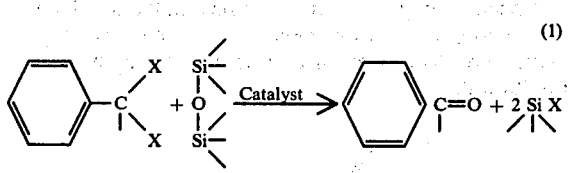

and

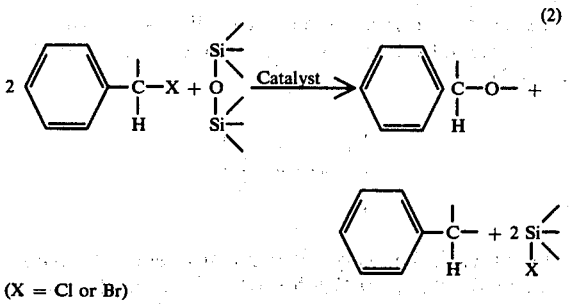

(X = Cl or Br)

In Equation 1, the free valences of the carbon atom are preferably bound to hydrogen or halogen; they can also, however, be bound to an aromatic moiety, preferably phenyl, or to a hydrocarbon moiety. The aromatic moieties forming in accordance with Equation 2 react preferably intermolecularly with one another, for example with the formation of diphthalidyl ether or dibenzyl ether.

In the case of the reaction with monohalogen methyl benzenes, benzyl trialkyl silyl ethers of the general formula

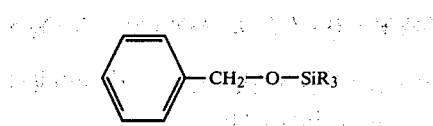

may form intermediately, in addition to the halogen alkyl silanes, in accordance with Equation 3.

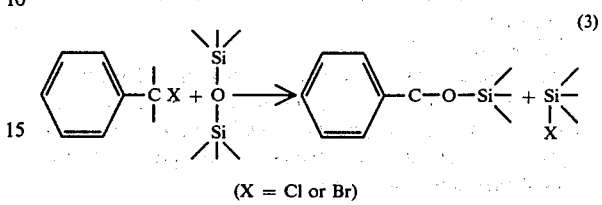

(X = Cl or Br)

In many cases the formation of this ether can be detected directly (e.g., by gas chromatography). Under the conditions of the reaction, however, the ether easily reacts further to form the above-named end products.

For the performance of the reaction of the invention, it is unimportant whether additional substituents are on the benzene nucleus, such as halogen or unsubstituted alkyl moieties.

The general Equations 1 and 2 show that 0.5 mol of the siloxane is used for each equivalent of removable halogen on the halogen methyl benzene where such compound has the formula

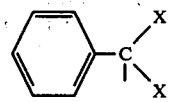

preferably there are employed between 0.4 and 0.6 mols of siloxane for each equivalent of removable halogen on the halogen methyl benzene. If the compound has the formula

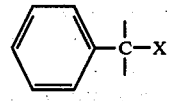

where X equals chlorine or bromine, there are employed at least 0.5 mols of siloxane for each equivalent of removable halogen. Preferably there are employed between 0.5 and 2.0 mols of siloxane per equivalent of removable halogen. It is understood in reciting the quantities of siloxane, that these quantities are recited on the basis that there is a single siloxane linkage. The quantities will change where the siloxane has multiple siloxane linkages.

If it is desired in accordance with Equation 3, to isolate the silyl ethers forming as intermediates, in this case one equivalent of the grouping

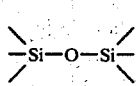

must be used for each monohalogen methyl benzene. Preferably, there are employed between 1.0 and 10.0 equivalents of such grouping for each monohalogen methyl benzene.

In the reaction of the invention, aromatic carboxylic acid chlorides, aromatic aldehydes or ketones or ethers form, depending on the degree of halogenation of the methyl group and depending on the employed amount of siloxane.

A large number of metals, elemental or in bound form, are suitable as catalysts for the process of the invention. Basically, all metals of the secondary group elements or of the fifth principal group of the periodic system of the elements have a more or less pronounced catalytic effect. Particularly effective metal catalysts in conjunction with the process of the invention are iron and nickel, manganese, molybdenum, vanadium, arsenic, antimony, bismuth, thallium, zinc and cadmium. They act not only when added in elemental form, preferably in the form of powder, or in the form of their compounds (as oxides, for example) or of their salts, such as for example acetyl acetonates, sulfates, sulfides, chlorides, acetates, silicates, phosphates, but also when added in alcoholate form. The chlorides are used preferably. These catalysts can be used in substance or, if they are soluble in one of the reactants or in the co-catalyst, they can be used in dissolved form. If these catalysts are used, the presence of a proton donor as co-catalyst is necessary for the start-up of the reaction, as an additional condition for the performance of the process of the invention. It is then advantageous to combine the catalyst with it.

Suitable catalysts are furthermore oxygen acids of sulfur. These include both inorganic and organic oxygen acids, which can also be substituted if desired. The following are given as examples: sulfuric acid, thiosulfuric acid, chlorosulfonic acid, p-toluenesulfonic acid.

Any substance from which a hydrogen cation can be cleaved can serve as the co-catalyst for the process of the invention, for example, water, any protonic acid, carboxylic acids, alcohols, etc. If the catalysts do not themselves have the co-catalytic property in addition to their catalytic activity, e.g., the acids of sulfur, or a water-of-crystallization in salts, e.g., $FeCl_3.6H_2O$, it is therefore advantageous to dissolve the soluble catalyst compounds before use, preferably in water or in aqueous acids; insoluble compounds, however, are to be used in substance, and the co-catalyst is then to be added separately, in order thus to start up the reaction.

The catalyst, as well as the co-catalyst if desired, is put into the reaction mixture at the beginning of the reaction. It is not necessary that the catalyst be present in solution in the reaction medium. Amounts of as little as $10^{-4}\%$ of the weight of the reaction mixture are effective. Even smaller amounts of the catalyst are also effective in many cases.

Preferably, the catalyst is added in amounts between $10^{-4}\%$ and 1% of the weight of the reaction mixture. Basically it is also possible to use larger amounts, but in general this results in no improvement or in only slight improvements.

The amount of the co-catalyst is of the same order of magnitude as that of the catalyst.

The reaction of the invention takes place in the temperature range between 90° and 220° C. The preferred temperatures are between 135° and 175° C. The reaction temperature is to be as high as possible above the boiling point of the chlorosilane that forms, so that the latter can be continuously distilled out in the course of the reaction.

The reaction takes place very rapidly. It is therefore recommendable to put one of the reactants, preferably the halogen methyl benzene, together with the catalyst and the co-catalyst if desired, into the reactor and to add the second reactant to the first reactant heated to the desired reaction temperature, it being advantageous also to heat the second reactant to the reaction temperature.

The halogen alkylsilane forming in the reaction is best distilled out as it forms. The second reactant is then preferably added at the same rate as the halogen alkyl silane is distilled out. The rate of input of the second reactant is therefore dependent upon the distillation capacity of the column through which the halogen silane is distilled out. However, care must be taken to see that the reaction is not interrupted, because otherwise fresh catalyst and/or co-catalyst must be added. As soon as the reaction has started up, therefore, a small amount of the second reactant should always be present in the reaction medium.

After the input of the second reactant is terminated in the method of procedure just described, the distillation of the halogen silane is terminated immediately thereafter. The halogen silane is produced in yields better than 90%, in a high purity, and it can be used directly for further processes.

The isolation of the aromatic carbonyl compounds or aromatic ethers, as the case may be, is then performed in a known manner, either by distillation, vacuum distillation if desired, or by crystallization. In the latter case, the reactor is one equipped with a stirrer for solids, such as a wall-riding anchor stirrer, and the reaction mixture is kept in constant movement during the reaction.

In general, a reactor is used which is simultaneously the body of a distillation column. The reactor furthermore contains an introduction tube reaching into the liquid phase of the starting compound initially placed in the reactor, for the purpose of introducing the second, liquid reaction component, which, if desired, can also be introduced in the form of a gas (preheated or evaporated, for example) through this introduction tube into the first reaction component.

The aromatic carbonyl compounds or ethers obtained in accordance with the invention are likewise produced in a better than 90% yield and in a purity which makes it possible to use them immediately without any additional purifying operations. If this product of the process is crystalline, and an especially pure product is required, all that is necessary is recrystallization.

The chloromethyl benzenes usable as starting products include compounds of the general formulas:

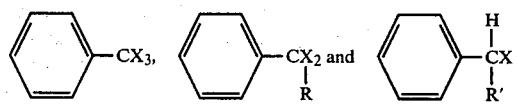

in which R represents hydrogen, an aryl moiety, preferably phenyl, or an alkyl or alkenyl moiety with preferably one to four carbon atoms, and R' is the same as R or an oxygen atom which is joined to the benzene nucleus by a carbonyl group. X represents chlorine or bromine. The benzene nucleus can furthermore be substituted one or more times by halogen moieties. Even compounds in which several halogen methyl groups are on the benzene nucleus can be used in accordance with the invention.

The following are examples of compounds which satisfy these formulae: benzal chloride, p-fluorobenzal chloride, p-chlorobenzal chloride, 2,4-dichlorobenzal chloride, p-bromobenzal chloride, benzotrichloride, 3-chlorobenzotrichloride, 4-chlorobenzotrichloride, 2,4-dichlorobenzotrichloride, 2,4,6-trichlorobenzotrichloride, p-bromobenzotrichloride, 3,5-dibromobenzotrichloride, 2,4-dibromobenzotrichloride, p-iodobenzotrichloride, fluorodichloromethylbenzene, α,α'-pentachloro-o-xylene, 1,3 [bis-trichloromethyl] benzene, 1,4 [bis-trichloromethyl] benzene, 1.4 [bis-trichloromethyl] 2,3,5,6-tetrachlorobenzene, 2,3,5,6-tetrabromo-α,α'-hexachloropxylene and diphenyldichloromethane.

In accordance with the invention, aldehydes or carboxylic acid chlorides or their derivatives are produced from aromatic chloromethyl compounds, such as for example benzaldehyde, p-fluorobenzaldehyde, p-chlorobenzaldehyde, 2,4-dichlorobenzaldehyde, p-bromobenzaldehyde, p-iodobenzaldehyde, benzoyl chloride, 3-chlorobenzoyl chloride, 4-chlorobenzoyl chloride, 2,4-dichlorobenzoyl chloride, 2,4,6-trichlorobenzoyl chloride, p-bromobenzoyl chloride, 3,5-dibromobenzoyl chloride, 2,4-dibromobenzoyl chloride, p-iodobenzoyl chloride, benzoyl fluoride, 3-chlorophthalide, di-phthalidyl ether, isophthalic acid dichloride, terephthalic acid dichloride, tetrachloroterephthalic acid dichloride, tetrabromoterephthalic acid dichloride, etc.

The siloxanes which are usuable include all liquid siloxanes which have the groups

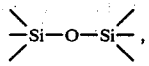

wherein the free valences of the silicon atom can be saturated by halogen, alkyl, alkenyl or another

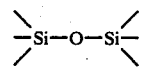

grouping. The following are to be considered as among these compounds: disiloxanes of the general formula $(R_{3-a}'' Cl_aSi)_2O$ wherein "a"=0-3, R"=alkyl or alkenyl with 1-4 carbon atoms; cyclopolysiloxanes of the general formula $(R_{2-b}'' Cl_bSiO)_c$ wherein "b"=0-2, and "c"=3-12 for monocyclic structure, as well as the corresponding rings of polycyclic, spirocyclic and spherocyclic structure; chain-polymeric dialkyl and dialkenyl polysiloxanes of the general formula $R_3''SiO-(R_2''SiO)_d$-$SiR_3''$ and branched siloxanes and/or polysiloxanes, having for example the general formula $R''Si[(OSiR_2''-)_dOSiR_3'']_3$ wherein d is the degree of polymerization from 1 to the highest values at which the polymer can still be delivered in liquid form, e.g. 5000.

Examples of individual compounds which come under this definition are hexachlorodisiloxane, tetramethyldichlorodisiloxane, hexamethyldisiloxane, hexaethyldisiloxane, hexamethylcyclotrisiloxane, octamethylcyclotetrasiloxane, decamethylcyclopentasiloxane, divinyltetrachlorodisiloxane, diisobutyltetrachlorodisiloxane, linear polydimethylsiloxanes of low to high degrees of polymerization and viscosities, polyvinylmethylsiloxanes, methyl-tris-trimethylsiloxysilane, tetrakis-trimethylsiloxysilane, branched polymethylsiloxanes, silicone oils, especially siloxane or silicone wastes, such as for example used heat transfer oils and hydraulic oils etc.

By the process of the invention, chlorosilanes and chloro-organosilanes are formed, such as for example tetrachlorosilanes, methyltrichlorosilane, vinyltrichlorosilane, propyltrichlorosilane, isobutyltrichlorosilane, dimethyldichlorosilane, vinylmethyldichlorosilane, trimethylchlorosilane, etc., depending on the siloxane put in. Branched siloxanes yield mixtures which have to be separated by distillation methods known for that purpose.

In order to more fully illustrate the nature of the invention and the manner of practicing the same, the following Examples are presented.

EXAMPLES

Example 1

Preparation of benzoyl chloride and tetrachlorosilane from benzotrichloride and hexachlorodisiloxane in the presence of Zinc(II) chloride ($ZnCl_2$)

In a two-liter four-necked flask heated by an oil bath and equipped with stirrer, internal thermometer, submerged gas introduction tube and a superimposed column (6 plates, diam. 50 mm, filling depth 250 mm, V4A drawn metal for vacuum distillation) having an automatic head, 1955 g (10 mol) of benzotrichloride (trichloromethylbenzene) is placed and heated at 148° C. Then the reaction is started by the addition of 1 ml of 50% solution of $ZnCl_2$ in water, while at the same time beginning the delivery of gaseous hexachlorodisiloxane through the gas introduction tube, which for this purpose is connected through an evaporator operating at 160° C. with a hexachlorodisiloxane supply tank disposed at a height of about 900 mm. A quantity of 2840 g (9.97 mol) is fed into the flask at a constant rate of about 350 g per hour.

Immediately after the reaction is started, the distillation of pure $SiCl_4$ (B.P. 57.6° C.) begins at a return ratio of 1, and ends immediately after the addition of the siloxane stops.

Then the receiver is replaced, and benzoyl chloride (B.P. 92° C. at 40 mbar (M.P. −1° C.) is distilled out in vacuo. The yield of benzoyl chloride amounts to 1348 g (96.3%) and that of tetrachlorosilane to 3305 g (98.4%).

EXAMPLE 2

Preparation of terephthalic acid dichloride and trimethylchlorosilane from α,α'-hexachloro-p-xylene and hexamethyldisiloxane in the presence of $MoO_3$ In a laboratory apparatus similar to that of Example 1, but with a ten-liter flask, 12510 g (40 mol) of α,α'-hexachloro-p-xylene is heated at 159° C. Then 0.5 g of $MoO_3$ is stirred in and the reaction is started by the addition of a little gaseous hydrogen chloride into the melt while simultaneously starting the delivery of gaseous hexamethyldisiloxane through the gas introduction tube as in Example 1. A total amount of 12974 g (79.9 mol) of hexamethyldisiloxane is fed in at a constant rate of approximately 1200 g per hour. Immediately after the start of the reaction, the distillation of pure trimethylchlorosilane (B.P. 57.7° C.) begins at a return ratio of 1, and terminates immediately after the end of the siloxane feed.

Then the condenser temperature in the column head is adjusted to 80° C. with a thermostat, the receiver is changed, and terephthalyl chloride (B.P. 119° C. at 18 mbar; M.P. 78° C.) is distilled out in vacuo.

The yield of terephthyl chloride amounts to 7922 g (97.5%) and the yield of trimethylchlorosilane is 17.26 kg (99.5%).

EXAMPLE 3

Preparation of 3-chlorophthalide and trimethylchlorosilane from α,α'-pentachloro-o-xylene and hexamethyldisiloxane in the presence of FeCl$_3$.6H$_2$O As in Examples 1 and 2, 11136 g (40 mol) of α,α'-pentachloro-o-xylene ([1-trichloromethyl-2-dichloromethyl]benzene) is heated at 141° C. Then the reaction is started by adding 1 ml of a 50% aqueous solution of FeCl$_3$.6H$_2$O while at the same time beginning the delivery of gaseous hexamethyldisiloxane. A total amount of 12970 g (79.9 mol) of hexamethyldisiloxane is put in at a constant rate of about 1200 g per hour. After every 30 minutes, 0.2 ml of 50% aqueous FeCl$_3$.6H$_2$O solution is added to the batch in process.

Immediately after the start of the reaction, the distillation of pure trimethylchlorosilane (B.P. 57.7° C.) begins, and it ends immediately after the end of the delivery of the siloxane. Then the condenser temperature at the top of the column is adjusted by a thermostat to 65° C., the receiver is changed, and 3-chlorophthalide (B.P. 102° C. at 2 mbar; M.P. 60°-61° C.) is distilled out in vacuo.

The yield of 3-chlorophthalide amounts to 6530 g (96.9%) and that of trimethylchlorosilane to 17.22 kg (99.3%).

The process takes place according to the following equation:

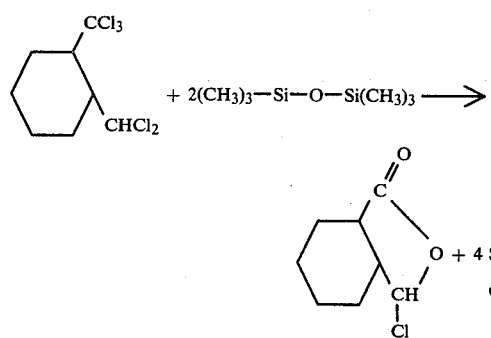

EXAMPLE 4

Preparation of diphthalidyl ether and trimethylchlorosilane from α,α'-pentachloro-o-xylene and hexamethyldisiloxane in the presence of FeCl$_3$.6H$_2$O In a thermostat-controlled, jacket-heated laboratory stirring vessel having a four-liter capacity for viscous and crystalline substances, equipped with a wall-riding anchor stirrer (83 rpm) and flow breakers, an internal temperature sensor, a submerged gas introduction tube and a superimposed column (approx. 8 plates, diam. 50 mm, depth of packing 250 mm, packing bodies 6 mm porcelain saddles) with an automatic head, 3340 g (12 mol) of α,α'-pentachloro-o-xylene is heated to 140° C. Then the reaction is started by the addition of 1 ml of 50% aqueous solution of FeCl$_3$.6H$_2$O while simultaneously beginning the delivery of gaseous hexamethyldisiloxane (as in Example 1). A total amount of 4872 g (30 mol) of hexamethyldisiloxane is put in at a constant rate of about 900 g per hour.

Immediately after the start of the reaction, the distillation of pure trimethylchlorosilane (B.P. 57.7° C.) begins at a return ratio of 1, and ends immediately after the end of the siloxane feed. The liquid reaction mixture begins to precipitate crystals after the addition of about 4 kg of hexamethyldisiloxane, and during the addition of the rest of the siloxane it is transformed to a dry crystal powder consisting of pure diphthalidyl ether which, after brief evacuation and flooding with nitrogen, has a melting point of 220° to 222° C.

The yield amounts to 1646 g (97%) of diphthalidyl ether and 6420 g (98.5%) of trimethylchlorosilane.

The process takes place according to the following reaction:

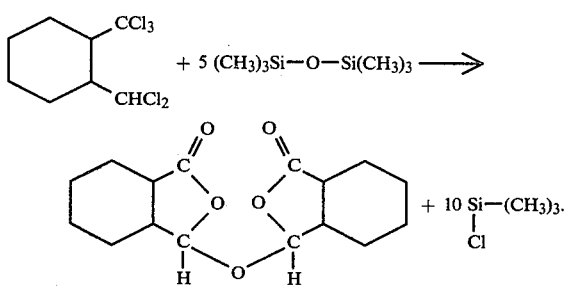

EXAMPLE 5

Preparation of p-chlorobenzaldehyde and trimethylchlorosilane from p-chlorobenzal chloride and hexamethyldisiloxane in the presence of TlCl$_3$ 1955 g (10 mol) of p-chlorobenzal chloride is heated to 166° C. as in Example 1. Then the reaction is started with 1 ml of 50% aqueous solution of TlCl$_3$, and the rest of the procedure is as described in Example 1, except that 1640 g (10 mol) of hexamethyl disiloxane is used as the second reaction component, which is fed in at a rate of about 230 g per hour. During the reaction, 2130 g of trimethylchlorosilane distills out (approx. 98% yield).

After the reaction has ended, the condenser temperature in the head of the column is adjusted by means of a thermostat to 50° C. and the p-chlorobenzaldehyde (M.P. 47°-48° C.) is distilled out in vacuo (B.P. 114° C. at 60 mbar; 1360 g=96.7%).

EXAMPLE 6

Preparation of 2,5-dichlorobenzaldehyde and trimethylchlorosilane from 2,5-dichlorobenzal chloride and hexamethyldisiloxane in the presence of H$_2$SO$_4$ 2300 g of 2,5-dichlorobenzal chloride is reacted as in Example 5, at 170° C., with 0.5 ml of concentrated H$_2$SO$_4$ as starter and catalyst. The product is 2126 g (approx. 98%) of trimethylchlorosilane and 1684 g (approx. 96.2%) of 2,5-dichlorobenzaldehyde (B.P. 129° C. at 20 mbar and 60° C. condenser temperature on account of the melting point of 56°-58° C.).

EXAMPLE 7

Preparation of tetrachloroterephthalic acid dichloride and a mixture consisting of trimethylchlorosilane and methyltrichlorosilane from perchloro-p-xylene (1,4-[bistrichloromethyl]2,3,5,6tetrachlorobenzene) and methyl-tristrimethylsiloxysilane in the presence of SbCl₅

As in Example 4, 4055 g (9 mol) of perchloro-p-xylene is stirred at 158° C. with 0.5 ml of SbCl₅, and the reaction is started with 1 ml of water while simultaneously beginning the input of 1860 g (6 mol) of MeSi[OSi(CH₃)₃]₃ in liquid form, preheated to 160° C., through the submerged tube at a constant rate of about 380 g per hour. During the reaction a mixture of trimethylchlorosilane and methyltrichlorosilane distills over at a head temperature of about 59° C., totaling approximately 2800 g (approx. 98%), in which the ratio of the two products, determined by gas chromatography, amounts to approximately 7:3.

After the cold stirring, evacuation to 20 mbar and crystallization at about 140° C., and flooding with nitrogen gas, 3040 g of tetrachlorophthalic acid dichloride is obtained from the reaction vessel in a yield of about 99%, having a melting point of 142°–143° C.

EXAMPLE 8

Preparation of p-bromobenzoyl chloride and dimethyldichlorosilane from p-bromobenzotrichloride and hexamethylcyclotrisiloxane in the presence of BiCl₃

As described in Example 1, 1646 g (6 mol) of p-bromobenzotrichloride is heated to 154° C., stirred with 0.5 BiCl₃, and the reaction is started with 1 ml of water while simultaneously beginning the delivery of 445 g (2 mol) of hexamethylcyclotrisiloxane (gassified by preheating to the reaction temperature).

During the reaction (approx. 4 hours), about 770 g of dimethyldichlorosilane (B.P. 70° C.) is distilled out in a virtually quantitative yield, at a return ratio of 1. Then, at a condensing temperature of about 42° C., 1245 g of p-bromobenzoyl chloride (M.P. 39°–40° C.) is distilled out in a yield of about 95%.

EXAMPLES 9 TO 12

Preparation of isophthalic acid dichloride and trimethylchlorosilane from α,α'-hexachloromxylene and hexamethyldisiloxane in the presence of the catalysts CdCl₂.H₂O, NiCl₂.6H₂O, MnCl₂.4H₂O and paratoluenesolfonic acid In the manner described in Example 1, four tests are performed, each with 1565 g (5 mol) of α,α'-hexachloro-m-xylene at about 150° C. and 1620 g (10 mol) of hexamethyldisiloxane. In each test, 1 ml of 50% aqueous solution of CdCl₂.H₂O, NiCl₂.6H₂O, MnCl₂.4H₂O or paratoluensulfonic acid is used as catalyst and starter. During the reaction trimethylchlorosilane (B.P. 57.7° C.) is distilled out. Then the isophthalic acid dichloride (B.P. 97° C. at 3 mbar, M.P. 40°–41° C.) is vacuum distilled at a condenser temperature of 44° C.

The experimental conditions and results are summarized in the following table:

| Example No. | Catalyst | Isophthalic acid dichloride product weight | Yield | Trimethylchlorosilane product weight | Yield |
|---|---|---|---|---|---|
| 9 | CdCl₂ . H₂O | 977 g | 96% | 2154 g | 99% |
| 10 | NiCl₂ . 6H₂O | 986 g | 97% | 2148 g | 99% |
| 11 | MnCl₂ . 4H₂O | 980 g | 96.5% | 2142 g | 98.5% |
| 12 |  | 975 g | 96% | 2132 g | 98% |

What is claimed is:

1. A process for the preparation of a halogen silane and an aromatic compound having at least one —C=O— or

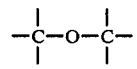

group, while simultaneously effecting cleavage of a siloxane which comprises contacting a compound having at least one aromatically bound mono and/or dihalogen methylene group or an aromatic compound having a mono-, di and/or trihalogen methyl group of the formula

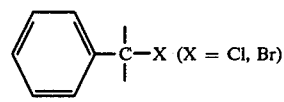

wherein the aromatic moiety can be optionally otherwise substituted, with a siloxane of the formula

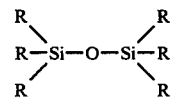

wherein each R moiety is independently selected from the group consisting of halogen, alkyl, alkenyl and O—SiR₃, wherein such R moiety is halogen, alkyl or alkenyl, wherein at least two of the R moieties can, together with the silicon atom to which they are attached, form a ring, at an elevated temperature in the presence of a catalytic amount of a metal or a metal compound, which metal is of the sub-group of elements or of the 5th principal group of the periodic system of the elements, together with a proton donor, or in the presence of a catalytic amount of an oxygen acid.

2. A process according to claim 1, wherein the process is effected at a temperature between 90° and 220° C.

3. A process according to claim 1, wherein the process is conducted by continuously distilling over halogen silane as it forms during the process.

4. A process according to claim 1, wherein an aromatic halogen methyl compound is reacted with siloxane, said aromatic halogen methyl compound is initially introduced into the reaction zone the temperature is increased to the reaction temperature and thereafter the catalyst and siloxane is added at a rate corresponding approximately to the rate at which the forming halogen silane is removed from the reaction mixture.

5. A process according to claim 4, wherein the forming halogen silane is removed from the reaction mixture by distillation.

6. A process according to claim 1, wherein a siloxane is reacted with a compound having at least one aromatically bound mono and/or dihalogen methylene group.

7. A process according to claim 1, wherein said siloxane is reacted with an aromatic compound containing a mono, di and/or trihalogen methyl group of the formula

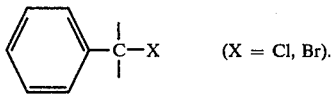   (X = Cl, Br).

8. A process according to claim 1, wherein at least one R moiety of the siloxane is alkyl of 1 to 4 carbon atoms.

9. A process according to claim 1, wherein at least one R moiety of the siloxane is an alkenyl group of 2 to 4 carbon atoms.

10. A process according to claim 1, wherein at least one R moiety of the siloxane is a halogen.

11. A process according to claim 1, wherein at least one R moiety has the formula O—Si—R, wherein the R of said O—SiR$_3$ moiety is halogen, alkyl or alkenyl.

12. A Process according to claim 1, wherein said siloxane is a di-siloxane.

13. A process according to claim 1, wherein said siloxane is a di-siloxane and said di-siloxane has the formula $(R_{3-a}''Cl_aSi)_2O$ wherein "a" is 0 to 3, R" is alkyl or alkenyl with 1 to 4 carbon atoms.

14. A process according to claim 1, wherein said siloxane is cyclopolysiloxane of the formula $(R_{2-b}''Cl_bSiO)_c$ wherein "b" equals 0-2, "c" equals 3-12 and R" is alkyl or alkenyl with 1 to 4 carbon atoms.

15. A process according to claim 1, wherein said siloxane has the formula $R_3''SiO—(R_3''SiO)_dSiR_3''$, wherein R" is alkyl or alkenyl with 1 to 4 carbon atoms and "d" is the degree of polymerization from 1 to the highest value which the polymer can still be delivered in the liquid form and said polysiloxane is in liquid form.

16. A process according to claim 1, wherin said siloxane is a polysiloxane of the formula $R''Si[(OSiR_2''-)_dOSiR_3]_3$ wherein R" is alkyl or alkenyl of 1 to 4 carbon atoms and "d" is the degree of polymerization from 1 to the highest value at which the polymer can still be delivered in liquid form and said polysiloxane is a liquid.

17. A process according to claim 1, wherein a siloxane is reacted with a chloromethyl benzene of the formula

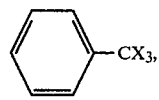

wherein X represents chlorine or bromine.

18. A process according to claim 1, wherein said siloxane is reacted with a chloromethyl benzene of the formula

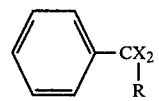

wherein X represents chlorine or bromine and R represents hydrogen, an aryl moiety or an alkyl or alkenyl moiety.

19. A process according to claim 1, wherein a siloxane is reacted with chloromethyl benzene of the formula

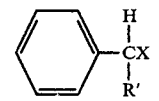

wherein
X represents chlorine or bromine and
R' represents aryl, alkyl or an alkenyl moiety or an oxygen atom which is joined to the benzene nucleus by a carbonyl group.

20. A process according to claim 1, wherein the catalyst comprises sulfur.

21. A process according to claim 1, wherein the catalyst comprises an oxygen acid.

22. A process according to claim 1, wherein said oxygen acid is selected from the group consisting of sulfuric acid, thiosulfuric acid, chlorosulfonic acid and p-toluenesulfonic acid.

23. A process according to claim 1, wherein the catalyst comprises a metal or compound of the metal and said metal is selected from the group consisting of iron, nickel, manganese, molybdenum, vanadium, arsenic, antimony, bismuth, thallium, zinc and cadmium.

24. A process according to claim 23, wherein said metal is in elemental form.

25. A process according to claim 23, wherein said metal is in the form of a compound.

26. A process according to claim 25, wherein said compound of said metal is a metal oxide, acetyl acetonate, sulfate, sulfide, chloride, acetate, silicate, phosphate or alcoholate.

27. A process according to claim 1, wherein said proton donor comprises a substance from which a hydrogen cation can be cleaved.

28. A process according to claim 27, wherein said proton donors are from the group consisting of water, a protonic acid, a carboxylic acid and an alcohol.

29. A process according to claim 27, wherein said proton donor is an acid of sulfur or a water-of-crystallization in salt form.

* * * * *